United States Patent [19]
Wachtler et al.

[11] Patent Number: 5,510,365
[45] Date of Patent: Apr. 23, 1996

[54] MEDICAMENTS CONTAINING 1-THIOCARBAMOYL-5-HYDROXY-PYRAZOLES AND THEIR USE AS AGENTS FOR COMBATING SEPTIC SHOCK

[75] Inventors: Peter Wachtler, Köln; Lutz Heuer, Krefeld; Michael Sperzel; Klaus G. Stünkel, both of Wuppertal, all of Germany

[73] Assignee: Bayer Aktiengesellschaft, Leverkusen, Germany

[21] Appl. No.: 286,080

[22] Filed: Aug. 4, 1994

[30] Foreign Application Priority Data

Aug. 11, 1993 [DE] Germany ............ 43 26 904.4
Apr. 28, 1994 [DE] Germany ............ 44 14 792.9

[51] Int. Cl.$^6$ ............... A61K 31/415; C07D 231/20
[52] U.S. Cl. ............... 514/407; 548/369.7; 548/366.7; 548/365.4; 548/365.7; 548/202; 548/312.4
[58] Field of Search ............... 548/369.7, 366.7, 548/365.4, 365.7; 514/407

[56] References Cited

U.S. PATENT DOCUMENTS 3,704,242  11/1972  Santiui et al. ............... 260/310

FOREIGN PATENT DOCUMENTS 0515934  5/1992  European Pat. Off. .

OTHER PUBLICATIONS

Chemical Abstracts, vol. 107, No. 17, Oct. 26, 1987, Abstract No. 154289r, K. Wegner et al.
Chemical Substances, 12th Collective Index vol. 106–115, 1987–1991 No. 78341CS & Archiv Der Pharmazie Bd. 320, Nov. 2, 1987, pp. 108–114 abstracting Arch. Pharm. 316 (1983) 2–6.
J. Pesticide Sci. 11, 205–212 (1986).
Reactions and Syntheses, Thieme Verlag, 1981, pp. 153, 440.
Oikawa et al., J. Org. Chem. 43, 2087 (1978).
Derwent Abstract of JP 54–115,374 (1974).
Derwent Abstract of JP 54–119,031 (1979).
K. Wegner, Sci Pharm. 51, 167–172 (1983).

*Primary Examiner*—Johann Richter
*Assistant Examiner*—Laura R. Cross
*Attorney, Agent, or Firm*—Sprung Horn Kramer & Woods

[57] ABSTRACT

The invention relates to the use of 1-thiocarbamoyl-5-hydroxypyrazoles of the general formula

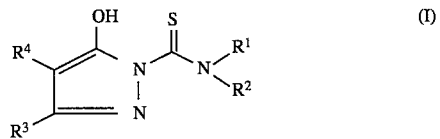

in which the substituents denote the radicals mentioned in the description, as pharmaceutical agents for combating septic shock and the consequences thereof.

6 Claims, No Drawings

MEDICAMENTS CONTAINING 1-THIOCARBAMOYL-5-HYDROXY-PYRAZOLES AND THEIR USE AS AGENTS FOR COMBATING SEPTIC SHOCK

The invention relates to the use of 1-thiocarbamoyl-5-hydroxypyrazoles of the general formula

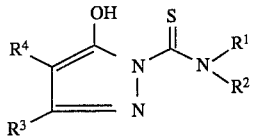

in which the substituents denote the radicals stated in the claims, as pharmaceutical agents for combating septic shock and the consequences thereof.

Thiocarbamoylpyrazoles represent a class of substances which is known in the protection of materials, since numerous representatives of this structural type have microbicidal properties and thus represent valuable material-protection agents, for example for the protection of paints or wood. This application is described in, for example, EP 515 934. In contrast, the use of thiocarbamoylpyrazoles as claimed in the present invention, in the pharmaceutical sector, especially for treating septic shock, has not been described hitherto.

The invention therefore relates to medicaments containing compounds of the general formula (I)

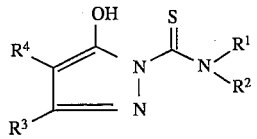

in which $R^1$ and $R^2$ independently of one another represent hydrogen, alkyl, cycloalkyl, alkenyl, aralkyl or aryl, the latter being unsubstituted or substituted with $C_{1-6}$-alkyl or halogen or $R^1$=H, $R^2$=$NH_2$, $R^3$ and $R^4$ independently of one another represent hydrogen or unsubstituted or substituted alkyl, alkenyl, alkinyl, cycloalkyl, cycloalkenyl, alkyl(cycloalkyl), alkenyl(cycloalkenyl), alkoxy, alkylthio, aralkoxy, aralkylthio, aralkyl, aryl, hetaryl, aryloxy, hetaryloxy, arylthio, hetarylthio, alkoxycarbonyl, alkoxycarbonylalkyl or cyanoalkyl, or $R^3$ and $R^4$ form a saturated or partially or completely unsaturated, unsubstituted or substituted ring, of 5 to 9 atoms in total, all of which are carbon atoms except for a maximum of two nitrogen, sulphur or oxygen atoms, or their metal complexes with metals such as, for example, iron, zinc, manganese, calcium, magnesium, potassium, sodium, lithium, lanthanum, platinum, gold and aluminium, and their physiologically acceptable salts with acids such as HCl, $HNO_3$, acetic acid, salicylic acid etc.

"Substituted" in the definitions of $R^3$ and $R^4$ denotes substitution by from one to seven—but not more than the number of H atoms present in the unsubstituted case— atoms or groups of atoms, selected from: F, Cl, Br, I, $NO_2$, CN, O-alkyl, S-alkyl, alkyl, —$CO_2$-alkyl, aryl and $NO_2$.

The following definitions apply here and below:

Alkyl=straight-chain or branched alkyl having 1 to 18 C atoms, such as Me, Et, n-, i-propyl, n-, i-, s- and tert-butyl, n-, i- and tert-pentyl, n-hexyl, n-octyl, n-nonyl, n-decyl, n-undecyl, n-dodecyl, n-tridecyl, n-tetradecyl, n-pentadecyl, n-hexadecyl, n-heptadecyl or n-octadecyl or their branched structural isomers.

These alkyl groups may be substituted by 1 to 15 halogen atoms, preferably chlorine and/or fluorine or CN.

The chain of C atoms may also be interrupted by 1 to 2 heteroatoms such as oxygen or sulphur, or groups of atoms such as N-Me, N-Et, —S(O), —$SO_2$, without its total number of atoms changing.

Alkenyl (+alkinyl) is defined as for alkyl, but altered to the extent that at least one and not more than three C—C single bonds have been replaced by a C—C double (triple) bond. The number of C atoms is at least three and is increased by at least two C atoms for each additional double bond (triple bond) added.

Cycloalkyl and cycloalkenyl groups comprise cycloalkyl with preferably 3 (5) to 7 C atoms, for example cyclopropyl, cyclobutyl, cycloheptyl, cyclopentyl, cyclopentenyl, cyclohexenyl and cyclohexyl; preferred substituted cycloalkyl groups comprise cycloalkyl which is substituted by 1 to 3 $C_1$–$C_4$-alkyl groups or 1 to 3 halogen atoms, such as chlorine and/or fluorine, examples being methylcyclohexyl, dimethylcyclohexyl, 1,3,3-trimethylcyclohexyl and 3-chlorocyclohexyl. Alkyl(cycloalkyl) and alkyl(cycloalkenyl) groups preferably contain 1 to 6 C atoms in the straight-chain or branched alkyl moiety and 3 to 7 C atoms in the cycloalkyl/alkenyl moiety, and are in particular (1-cyclopentyl)methyl, (1-cyclopentenyl)methyl, (1-cyclohexenyl)methyl, (1-cyclohexyl)methyl and (1-cyclopropyl)methyl.

Alkoxycarbonyl represents straight-chain or branched alkoxycarbonyl having preferably 1 to 6 C atoms in the alkoxy radical, for example methoxycarbonyl, ethoxycarbonyl, n- and i-propoxycarbonyl, n-, i-, sec- and tert-butoxycarbonyl, and hexyloxycarbonyl. Analogous comments apply to the alkoxycarbonylalkyl groups.

Aralkyl preferably contains 1 to 6, in particular 1 to 4 C atoms in the straight-chain or branched alkyl moiety and preferably phenyl or naphthyl as the aryl moiety. Examples of such aralkyl groups include benzyl, α-methylbenzyl, α,α-dimethylbenzyl, 2-phenethyl, and α- and β-naphthylmethyl. These aralkyl radicals may carry 1 to 3 substituents from the series consisting of halogen (especially chlorine and/or fluorine), nitro, cyano or unsubstituted or halogenated $C_1$–$C_4$-alkyl or $C_1$–$C_4$-alkoxy, for example methyl, ethyl, trifluoromethyl, difluorochloromethyl, difluoromethyl, trichloromethyl, methoxy, ethoxy, trifluoromethoxy, difluorochloromethoxy and difluoromethoxy, or unsubstituted or halogenated $C_1$–$C_4$-alkylmercapto, for example methylmercapto, trifluoromethylmercapto or difluorochloromethylmercapto.

The term aryl denotes unsubstituted or substituted aryl having preferably 6 to 12 C atoms in the aryl moiety. Preferred examples include phenyl, biphenyl and naphthyl. The aryl groups may carry 1 to 3 substituents from the series consisting of halogen (especially chlorine and/or fluorine), $C_1$–$C_6$-alkyl, $C_1$–$C_6$-alkoxy or thioalkoxy, halogeno-$C_1$–$C_2$-alkyl (such as trifluoromethyl or difluoromethyl), cyano, nitro, $C_1$–$C_6$alkoxycarbonyl or amino.

The term alkoxy denotes straight-chain or branched alkoxy having preferably 1 to 12, in particular 1 to 4 C atoms. Preferred examples include methoxy, ethoxy, n- and i-propoxy, n-, i-, sec- and tert-butoxy, pentoxy, hexoxy, heptoxy, octoxy, nonoxy and decoxy. The alkoxy groups may be substituted by 1 to 3 halogen atoms (Cl, F), preferably: O—$CF_3$, O—$CHF_2$, O—$CF_2$—O, O—$CF_2CF_2$—$O_3$ O—CFCL—CFCL—O.

Alkylthio represents straight-chain or branched alkylthio having preferably 1 to 12 C atoms. Preferred examples include methylthio, ethylthio, n- and i-propylthio, n-, i-, sec- and tert-butylthio, n-pentylthio and its isomers such as 1-, 2- and 3-methyl-butylthio. The alkylthio groups may be substituted by 1 to 3 halogen atoms (preferably chlorine and/or fluorine); preferred examples of these are di- and trifluoromethylthio and difluorochloromethylthio.

Aralkoxy preferably contains 1 to 6 C atoms in the straight-chain or branched alkyl moiety and preferably phenyl as aryl moiety. Preferred examples are benzyloxy and phenethyloxy. The aralkoxy groups may be substituted by 1 to 3 halogen atoms (preferably chlorine and/or fluorine) or by a $C_1$–$C_4$-alkyl group.

Cyanoalkyl is as alkyl (1 to 6) but substituted by cyano, preferably terminally.

Hetaryl: furyl, thienyl, thiazolyl, pyrazolyl, pyrrolyl, imidazolyl, triazolyl, unsubstituted or with 1 to 2 halogen or with alkyl, alkoxy or thioalkoxy substituents.

Halogen: F, Cl, Br, I.

Aralkylthio preferably contains 1 to 6 C atoms in the straight-chain or branched alkyl moiety and preferably phenyl as aryl moiety. The preferred example is benzylthio. The aralkylthio groups may be substituted by 1 to 3 halogen atoms (preferably chlorine and/or fluorine) or by a $C_1$–$C_4$-alkyl group.

Aryloxy preferably contains 1 to 10 C atoms in the aryl moiety. Preferred examples are phenoxy and naphthoxy. The aryloxy groups may carry 1 to 3 substituents from the series consisting of halogen (preferably chlorine and/or fluorine), $C_1$–$C_4$-alkyl, halogeno-$C_1$–$C_2$-alkyl (such as di- and trifluoromethyl), cyano, nitro or amino.

Arylthio preferably contains 6 to 10 C atoms in the aryl moiety. Preferred examples are phenylthio and naphthylthio. The arylthio groups may carry the substituents listed under "aryloxy".

Preferred examples of 1, ω-$C_3$–$C_6$-alk(en)ylene radicals include 1,3-propylene, 1,4-butylene and 1,4-butadien(1, 3)ylene.

Preferred compounds of the formula (I)

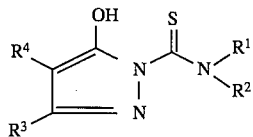

are those in which

R$^1$ denotes hydrogen or unsubstituted or substituted alkyl, alkenyl or aryl,

R$^2$ denotes hydrogen,

R$^3$ denotes hydrogen or unsubstituted or substituted $C_1$–$C_8$-alkyl, cycloalkyl, alkenyl, aralkyl or aryl, and R$^4$ denotes hydrogen or unsubstituted or substituted alkyl, cycloalkyl, alkenyl, aralkyl or aryl.

Particularly preferred compounds of the formula (I) are those in which

R$^1$ and R$^2$ denote hydrogen,

R$^3$ denotes unsubstituted or substituted $C_1$–$C_6$-alkyl, aralkyl or aryl, and R$^4$ denotes hydrogen or unsubstituted or substituted alkyl, aralkyl or aryl.

Very particularly preferred compounds of the formula (I) are those in which

R$^1$ and R$^2$ denote hydrogen,

R$^3$ denotes unsubstituted or substituted $C_1$–$C_6$-alkyl or aralkyl, and

R$^4$ denotes hydrogen, unsubstituted or substituted $C_1$–$C_6$-alkyl or aralkyl.

The compounds I to be used in accordance with the invention may be present as various tautomers (see below), including their tautomeric pyrazol-5-one form.

The compounds I to be used in accordance with the invention, and processes for their preparation, are known. For instance, published Japanese Patent Applications 79/115 374 and 79/119 031 describe 3-mono- and 3,4-disubstituted 1-thiocarbamoyl-5-hydroxy-pyrazoles which are active against plant diseases. They are said in particular to possess fungicidal action; cf. also J. Pesticide Sci. 11, 205–212 (1986).

Arch. Pharm. 316 (1983) 2–6 and Sci. Pharm. 51 (2) (1982) 167–172 disclose 4-mono- and 3,4-disubstituted 1-thiocarbamoyl-5-hydroxy-pyrazoles which are used as intermediates in the production of preparations having an antihistamine action.

EP 515 934 claims the use of 1-thiocarbamoyl-5-hydroxy-pyrazoles as material-protection agents.

To the extent that the compounds are still new, they can be prepared by analogy with the known preparation methods. Conventionally, an α-formylacetic ester or an α-formylacetamide or a β-ketoacetic ester or a β-ketoacetamide is reacted with a substituted or unsubstituted thiosemicarbazide. This condensation reaction takes place in accordance with the following equation (demonstrated using ethyl β-ketoacetate as the β-diketo starting product):

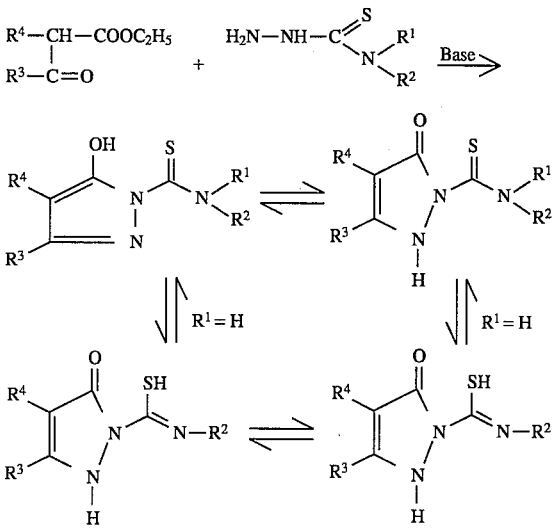

In the above formula, the substituents R$^1$ to R$^2$ have the definitions given above with respect to the compounds of the formula I.

0.8 to 1.0 mol of thiosemicarbazide is preferably reacted per mole of α-formylacetic acid derivative or per mole of β-diketo compound.

To facilitate the ring closure reaction, it is advantageous to add bases such as sodium hydroxide, potassium hydroxide or potassium tert-butylate. The base is preferably added in an amount approximately equivalent to the α-formylacetic acid derivative or the β-diketo compound.

The condensation may, if desired, be carried out in the presence of a solvent; solvents which have proved to be particularly suitable are alcohols such as ethanol or aromatic hydrocarbons such as toluene.

The condensation reaction can be carried out within a relatively large temperature range. For the first step of thiosemicarbazone formation, the temperatures may be from 20° to 110° C., preferably between 60° and 90° C. The cyclocondensation reaction, which takes place after the addition of base, can be carried out at temperatures from 20° to 100° C., preferably from 20° to 40° C. Since in many cases the addition of base is an exothermic procedure, cooling may be necessary in this step of the reaction.

The 1-thiocarbamoyl-5-hydroxy-pyrazoles can be isolated from the reaction mixtures by known methods. The general procedure is to free the reaction mixtures from solvent and to treat the residue with aqueous hydrochloric acid. The pyrazoles which precipitate in this procedure are separated off by filtration with suction. However, it is also possible to pour the reaction mixture directly into a large excess of dilute hydrochloric acid and to filter off the precipitated pyrazoles.

The starting compounds required for the preparation of the compounds I to be used in accordance with the invention, these starting compounds being namely the α-formylacetic esters or amides and the unsubstituted or α-substituted β-ketoacetic esters or amides, and the unsubstituted or substituted thiosemicarbazides, are either known compounds or can be prepared in analogy to known compounds by methods described earlier. In this context the following methods are useful: Tietze, Eicher, Reaktionen und Synthesen [Reactions and Syntheses], Thieme Verlag 1981, p. 153, 440; Oikawa, J. Org. Chem., 43, 2087 (1978).

As already mentioned above, some of the compounds I to be used in accordance with the invention are new. The invention therefore relates furthermore to compounds of the formula (II)

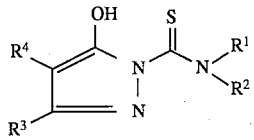

in which

R$^1$ and R$^2$ denote H, alkenyl or aryl, with the proviso that R$^1$ and R$^2$ are not simultaneously hydrogen, and R$^3$ and R$^4$ have the definitions given above with regard to the compounds of the formula (I).

Materials and methods
Endotoxic shock

B$_6$D$_2$F$_1$ mice are pretreated with galactosamine (600 mg/kg) and endotoxic shock is initiated with LPS (S. abortus equi, 0.01 μg/mouse). The mice die 8 to 24 hours after administration of LPS. The substances are given intravenously, subcutaneously, intraperitoneally or orally one hour before administration of LPS.

TNFα activity in serum

NMRI mice are treated with the substances one hour before administration of LPS. 1.5 hours after initiating the shock, blood samples are taken from which serum is obtained and the serum samples are frozen at −70° C. until testing. The TNFα serum activity is determined by a modified method of Espevik et al. (J. Immunol. Methods 956:99, 1986), which is based on the cytolysis of TNFα-sensitive cells (WEHI-164/13): 5×10$^4$ cells are incubated overnight in FCS-RPMI medium in 96-well plates. Subsequently the cells are incubated with the serum samples in various concentrations (overnight at 37° C. and 7% CO$_2$). The control sera employed are from untreated mice or from mice treated only with LPS. After the incubation steps the cells are stained.

Action of thiocarbamoylpyrazolones

The action of thiocarbamoylpyrazolones was demonstrated after a single intravenous, subcutaneous, intraperitoneal or oral administration.

| Example | Inhibition of endotoxic shock in mice (mortality) |
|---------|---------------------------------------------------|
| 2/005   |                                                   |
| 2/007   |                                                   |
| 2/011   |                                                   |
| 2/012   | ≦10 mg/kg iv                                      |
| 2/013   |                                                   |
| 3/035   |                                                   |
| 4/004   |                                                   |
| 10/007  |                                                   |

The prevention of mortality by the thiocarbamoylpyrazolones is correlated with the inhibition of TNFα activity in serum (Examples: 3/035 and 2/036 at 10 mg/kg).

EXAMPLES

No. 7 from Table 1 (1/007)

10.3 g (0.06 mol) of ethyl α-formyl-hexanoate and 5.5 g (0.06 mol) of thiosemicarbazide are placed in 200 ml of ethanol and stirred at 80° C. for 3 hours.

The mixture is then brought to room temperature and 6.9 g of potassium tert-butylate are added with stirring, after which stirring is continued at room temperature for 4 hours. The contents of the flask are then stirred into a mixture of 800 ml of water and 50 ml of conc. hydrochloric acid, and the resulting precipitate is filtered off with suction. The product is washed thoroughly with water and then left in a drying cabinet until constant weight is reached. The compound can be purified by recrystallization from ethanol.

Yield: 9.4 g (80.3% of theory) m.p.: 139°–141° C.

In the same way, from the corresponding α-formyl-carboxylic esters, the 4-substituted 1-thiocarbamoyl-5-hydroxypyrazoles listed in the following Table 1 can be obtained.

TABLE 1

R$^1$ = R$^2$ = R$^3$ = H

| Ex. No. | R$^4$ | m.p. |
|---------|-------|------|
| 1 | H— | |
| 2 | Me— | 164–165° C. |
| 3 | Et— | 144–145° C. |
| 4 | n-Pr— | 146–147° C. |
| 5 | i-Pr— | |
| 6 | c-Pr— | |
| 7 | n-Bu— | 139–141° C. |
| 8 | i-Bu | 128–131° C. |
| 9 | s-Bu— | |
| 10 | t-Bu— | |
| 11 | n-C$_5$H$_4$ | |
| 12 | Me$_2$CHCH$_2$— | 153–154° C. |
| 13 | Me$_2$CH(Me)CH$_2$— | |

TABLE 1-continued $R^1 = R^2 = R^3 = H$

Structure: $R^4$-C(OH)=CH-N(H)-N=C(S)-NH$_2$ (with R⁴ and H on the alkene, OH on carbon bearing thiosemicarbazide-type group)

| Ex. No. | R⁴ | m.p. |
|---|---|---|
| 14 | (CH₃)₂CH-CH(CH₃)-CH₂- | |
| 15 | (CH₃)(CH₃CH₂)C(CH₃)-CH₂- | |
| 16 | (CH₃)₂CH-CH₂-CH₂-CH(CH₃)- | |
| 17 | (CH₃)₂CH-CH(CH₃)-CH(CH₃)-Me | |
| 18 | (CH₃)₂CH-CH₂-CH(CH₃)-Me | |
| 19 | (CH₃)₂CH-CH₂-CH₂-CH₂- | |
| 20 | (CH₃)(CH₃CH₂)CH-CH(CH₃)-CH₂- | |
| 21 | CH₃-CH₂-CH₂-CH(CH₃)-CH₂- | |
| 22 | (CH₃)₂CH-CH(CH₃)-CH(CH₃)-CH₂- | |
| 23 | Me-(CH₂)₄-CH₂- | 136–137° C. |
| 24 | (CH₃)₂CH-CH₂-CH₂-CH₂-CH₂- | |
| 25 | CH₃-CH₂-CH(CH₃)-CH₂-CH₂-CH₂- | |
| 26 | CH₃-CH₂-CH₂-CH(CH₃)-CH₂-CH₂- | |
| 27 | CH₃-CH₂-CH₂-CH₂-CH(CH₃)-CH₂- | |
| 28 | CH₃-CH₂-CH₂-CH₂-CH₂-CH(CH₃)- | |
| 29 | (CH₃)₂CH-CH₂-CH₂-CH₂-CH(CH₃)- | |
| 30 | cyclopropyl-CH₂-CH₂- | |
| 31 | cyclopropyl-CH₂- | |
| 32 | 1-fluorocyclopropyl-CH₂- | |
| 33 | 1-chlorocyclopropyl-CH₂- | |
| 34 | 1-cyanocyclopropyl-CH₂- | |
| 35 | NC-CH₂-CH₂- | |
| 36 | CF₃- | |
| 37 | CF₃-CF₂- | |
| 38 | CF₃-CF₂-CF₂- | |
| 39 | CF₂=CF-CF₂-CH₂- (CF₂-CF₂-CH₂-) | |
| 40 | CF₃-CF₂-CF₂-CH₂- | |
| 41 | CH₂=CH-CH₂- | 134–135° C. |
| 42 | (CH₃)₂C=CH-CH₂- | |
| 43 | CH₃-CH=C(CH₃)-CH₂- | |
| 44 | (CH₃)₂C=C(CH₃)-CH₂- | |
| 45 | CH₂=CH-C(CH₃)₂-CH₂- | |
| 46 | CH₃-CH=CH-CH(CH₃)- | |
| 47 | CH₃-C(CH₃)=C(CH₃)-CH(CH₃)- | |
| 48 | CH₃-C(CH₃)=CH-CH(CH₃)-Me | |
| 49 | (CH₃)₂C=CH-CH₂-CH₂- | |
| 50 | CH₃-CH=C(CH₃)-CH₂-CH₂- | |
| 51 | CH₃-CH₂-CH=C(CH₃)-CH₂- | |

TABLE 1-continued $R^1 = R^2 = R^3 = H$ (structure: $R^4$-C(OH)=CH-CH=N-NH-C(=S)-NH$_2$)

| Ex. No. | R⁴ | m.p. |
|---|---|---|
| 52 | (CH₃)₂C=C(CH₃)-CH(CH₃)-CH₂— | |
| 53 | Me-CH=CH-CH₂-CH₂-CH₂— | |
| 54 | (CH₃)₂C=CH-CH₂-CH₂-CH₂— | |
| 55 | Me-CH=C(Me)-CH₂-CH₂— | |
| 56 | Me-CH₂-CH=C(Me)-CH₂-CH₂— | |
| 57 | Me-CH₂-CH₂-C(Me)=CH-CH₂— | |
| 58 | Me-CH₂-CH=CH-CH₂-CH(Me)- | |
| 59 | Me-CH(Me)-CH=CH-CH₂-CH(Me)- | |
| 60 | Me-C(Cl)=CH-CH₂— | |
| 61 | Cl-C(Cl)=CH-CH₂— | |
| 62 | Cl₂C=C(Cl)-CH₂— | |
| 63 | Me-C(Cl)=C(Me)-C(Me)H-CH₂— | |
| 64 | Me-C(Cl)=C(Cl)-CH(Me)-Me | |
| 65 | Cl₂C=C(Cl)-CH(Me)-CH₂-Me | |
| 66 | Cl₂C=CH-CH(Me) | |
| 67 | Cl₂C=CH-CH₂-CH₂— | |
| 68 | Cl-CH=C(Cl)-CH₂-CH₂— | |
| 69 | Me-CH=C(Cl)-CH(Me)-CH₂— | |
| 70 | Me-C(Cl)=C(Cl)-CH₂-CH₂— | |
| 71 | Me-CH₂-C(Cl)=C(Cl)-CH₂— | |
| 72 | Cl₂C=CH-CH₂-CH₂-CH₂— | |
| 73 | Cl-CH=C(Cl)-CH₂-CH₂-CH₂— | |
| 74 | Me-CH₂-C(Cl)=CH-CH₂-CH₂— | |
| 75 | Me-CH₂-CH₂-C(Cl)=CH-CH₂— | |
| 76 | Me-C(Cl)=CH-CH₂-CH₂-CH(Me)- | |
| 77 | (CH₃)₂C=CH-CH(Cl)-CH₂-CH₂- | |
| 78 | n-C₇H₁₅ | |
| 79 | n-C₈H₁₇ | |
| 80 | n-C₉H₁₉ | |
| 81 | n-C₁₀—H₂₁ | 128–131° C. |
| 82 | n-C₁₁H₂₃ | |
| 83 | n-C₁₂H₂₅ | |
| 84 | n-C₁₃H₂₇ | |
| 91 | cyclohexyl | 157–158° C. |
| 92 | cyclohex-2-enyl | |

TABLE 1-continued $R^1 = R^2 = R^3 = H$

[Structure: R⁴-C(=CH-)-C(OH)=N-NH-C(S)-NH₂]

| Ex. No. | R⁴ | m.p. |
|---|---|---|
| 93 | cyclohexyl-CH₂— | 185° C. |
| 94 | cyclohexenyl-CH₂— | |
| 95 | 3-(CO₂Et)-phenyl | 165–167° C. |
| 96 | phenyl | 176° C. |
| 97 | 2-Cl-phenyl | 231–236° C. |
| 98 | 3-Cl-phenyl | 168–169° C. |
| 99 | 4-Cl-phenyl | 231–232° C. |
| 100 | 2,4-diCl-phenyl | 171–173° C. |
| 101 | 2,3-diCl-phenyl | |
| 102 | 3,4-diCl-phenyl | |
| 103 | 2,5-diCl-phenyl | |
| 104 | 2,6-diCl-phenyl | |
| 105 | 2-F-phenyl | 157–158° C. |
| 106 | 4-Br-phenyl | 194–195° C. |
| 107 | 2-Me-5-F-phenyl | 171–172° C. |
| 108 | 4-I-phenyl | |
| 109 | 2-CF₃-phenyl | 174–175° C. |
| 110 | 2-OMe-phenyl | 150° C. |
| 111 | 3-MeO-phenyl | 162–163° C. |
| 112 | 4-MeO-phenyl | 240–242° C. |

TABLE 1-continued $R^1 = R^2 = R^3 = H$

Structure: $R^4$-CH=C(OH)-NH-N(=)-C(=S)-NH_2 (with H on the CH)

| Ex. No. | $R^4$ | m.p. |
|---|---|---|
| 113 | 2,5-dimethoxyphenyl (OMe at 2 and 5) | |
| 114 | 2,3-dimethoxyphenyl | 263–265° C. |
| 115 | 2-methyl-5-methoxyphenyl | 167° C. |
| 116 | 4-methyl-2-methoxyphenyl | |
| 117 | biphenyl-4-yl | 284–286° C. |
| 118 | biphenyl-2-yl | |
| 119 | naphthalen-1-yl | 174–176° C. |
| 120 | naphthalen-2-yl | 236–237° C. |
| 121 | 2-methylphenyl (o-tolyl) | 200° C. decomp. |
| 122 | 3-methylphenyl (m-tolyl) | 177° C. |
| 123 | 4-methylphenyl (p-tolyl) | 197–198° C. |
| 124 | 2,3-dimethylphenyl | |
| 125 | 2,5-dimethylphenyl | 178–179° C. |
| 126 | 2,4-dimethylphenyl | |
| 127 | 2,6-dimethylphenyl | |
| 128 | 3,4-dimethylphenyl | |
| 129 | 3,5-dimethylphenyl | |
| 130 | benzyl (PhCH$_2$–) | 161–162° C. |

TABLE 1-continued
R¹ = R² = R³ = H
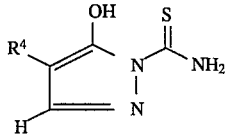
| Ex. No. | R⁴ | m.p. |
|---|---|---|
| 131 | 2-F-C₆H₄-CH₂- | 170–172° C. |
| 132 | 2-Cl-C₆H₄-CH₂- | 152–154° C. |
| 133 | 3-Cl-C₆H₄-CH₂- | 173° C. |
| 134 | 4-Cl-C₆H₄-CH₂- | 166–167° C. |
| 135 | 2,4-Cl₂-C₆H₃-CH₂- | 182° C. |
| 136 | 2,3-Cl₂-C₆H₃-CH₂- | 176° C. |
| 137 | 3,4-Cl₂-C₆H₃-CH₂- | |
| 138 | 3,5-Cl₂-C₆H₃-CH₂- | |
| 139 | 2,5-Cl₂-C₆H₃-CH₂- | |
| 140 | 2,6-Cl₂-C₆H₃-CH₂- | |
| 141 | 4-Me-C₆H₄-CH₂- | 186° C. |
| 142 | 3-Me-C₆H₄-CH₂- | |
| 143 | 2-Me-C₆H₄-CH₂- | |
| 144 | 2-OMe-C₆H₄-CH₂- | |
| 145 | 3-OMe-C₆H₄-CH₂- | |
| 146 | 4-MeO-C₆H₄-CH₂- | 160° C. |
| 147 | 4-ᵗBu-C₆H₄-CH₂- | >200° C. |
| 148 | C₆H₅-CH(Me)- | 161–163° C. |
| 149 | 4-Cl-C₆H₄-CH(Me)- | |
| 150 | 1-naphthyl-CH₂- | 169–170° C. |
| 151 | 2-naphthyl-CH₂- | |
| 152 | C₆H₅-S- | 213–214° C. |

TABLE 1-continued

R¹ = R² = R³ = H

| Ex. No. | R⁴ | m.p. |
|---|---|---|
| 153 | 4-Cl-C₆H₄-S— | 207–208° C. |
| 154 | C₆H₅-O— | 204° C. |
| 155 | 4-Cl-C₆H₄-O— | |
| 156 | C₆H₅-CH₂-S— | 177–178° C. |
| 157 | C₆H₅-CH₂-O— | 214° C. |
| 158 | 4-Cl-C₆H₄-CH₂-S— | |
| 159 | MeO-C(O)- | |
| 160 | EtO-C(O)- | 187° C. |
| 161 | n-PrO-C(O)- | |
| 162 | n-BuO-C(O)- | |
| 163 | Me—O— | 149–150° C. |
| 164 | Et—O— | |
| 165 | n-Pr—O— | |
| 166 | n-Bu—O— | |
| 167 | Me—S—CH₂— | |
| 168 | Et—S—CH₂— | |
| 169 | n-Pr—S—CH₂— | |
| 170 | n-Bu—S—CH₂— | |
| 171 | i-Pr—S—CH₂— | |
| 172 | n-C₅H₄—S—CH₂— | |
| 173 | Me—S—(CH₂)₂— | |
| 174 | Et—S—(CH₂)₂— | |
| 175 | n-Pr—S—(CH₂)₂— | |
| 176 | n-Bu—S—(CH₂)₂— | |
| 177 | Me—O—CH₂— | |
| 178 | Et—O—CH₂— | |
| 179 | n-Pr—O—CH₂— | |
| 180 | n-Bu—O—CH₂— | |
| 181 | n-Pr—O—CH₂— | |
| 182 | n-C₅H₄—O—CH₂— | |
| 183 | Me—O—(CH₂)₂— | |
| 184 | Et—O—(CH₂)₂— | |
| 185 | n-Pr—O—(CH₂)₂— | |
| 186 | n-Bu—O—(CH₂)₂— | |
| 187 | Ph—S—CH₂— | |
| 188 | Ph—O—CH₂— | |
| 189 | Ph—CH₂—S—CH₂— | |
| 190 | Ph—CH₂—O—CH₂— | |
| 191 | MeO-C(O)-CH₂— | |
| 192 | EtO-C(O)-CH₂— | 135–136° C. |
| 193 | 4-F-C₆H₄— | 145–6° C. |
| 194 | 2-furyl | |
| 195 | 2-thienyl | |
| 196 | 3-furyl | |
| 197 | 3-thienyl | |
| 198 | 5-methyl-2-furyl | |
| 199 | 5-methyl-2-thienyl | |
| 200 | 3-chloro-1-pyrazolyl | 200° C. decomp. |
| 201 | 4-Br-C₆H₄-CH₂— | 170–171° C. |

TABLE 1-continued $R^1 = R^2 = R^3 = H$

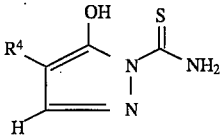

| Ex. No. | $R^4$ | m.p. |
|---|---|---|
| 202 | 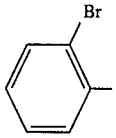 Br | 162–163 |
| 203 | 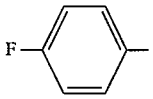 F | 174–175° C. |
| 204 | 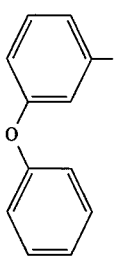 | 148–149° C. |
| 205 | n-C$_{17}$—H$_{39}$ | 150–154° C. |
| 206 | 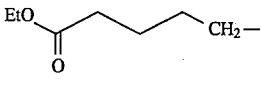 EtO—C(O)—...—CH$_2$— | |
| 207 | 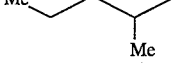 Me...Me | |

Example 4 from Table 2 (2/004)

(3-mono-substituted compounds)

4.6 g (0.05 mol) of thiosemicarbazide and 7.9 g (0.05 mol) of ethyl butyrylacetate together with 100 ml of ethanol are maintained at reflux temperature for 3 hours. The mixture is then left to cool to room temperature, and 5.9 g (0.05 mol, 97%) potassium tertbutylate are added in portions with stirring, after which stirring is continued at room temperature for 4 hours. The contents of the flask are then stirred into a mixture of 800 ml of water/50 ml of conc. HCl, and the resulting precipitate is filtered off with suction. After thorough washing with water the moist product is left in a drying cabinet (50 mbar/60° C.) until constant weight is reached.

Yield: 6.9 g (74.5% of theory) m.p.: 160°–161° C., colourless solid

In the same way, from the corresponding ethyl acylacetates, the 3-substituted 1-thiocarbamoyl-5-hydroxypyrazoles listed in the following Table 2 can be obtained.

The pyrazoles obtained are characterized by melting point determination.

TABLE 2

$R^1 = R^2 = R^4 = H$

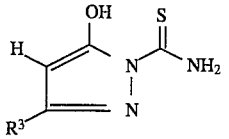

| Ex. No. | $R^3$ | m.p. |
|---|---|---|
| 1 | H— | |
| 2 | Me— | 178° C. |
| 3 | Et— | 154–158° C. |
| 4 | n-Pr— | 160–161° C. |
| 5 | i-Pr— | 153° C. |
| 6 | c-Pr— | 158° C. |
| 7 | n-Bu— | 148° C. |
| 8 | i-Bu | 153° C. |
| 9 | s-Bu— | 145–146° C. |
| 10 | t-Bu— | |
| 11 | n-C$_5$H$_4$ | 149° C. |
| 12 | 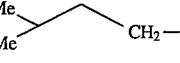 | 151° C. |
| 13 | 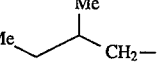 | 142° C. |
| 14 | 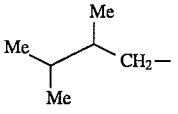 | |
| 15 | 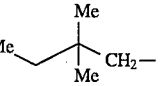 | |
| 16 | 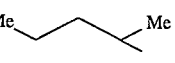 | 137° C. |
| 17 | 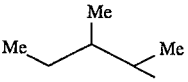 | |
| 18 | 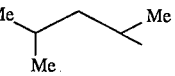 | |
| 19 | 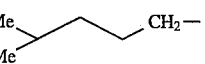 | |
| 20 | 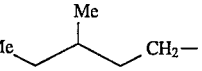 | |
| 21 | 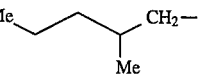 | |
| 22 | 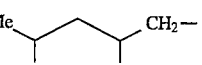 | |
| 23 | 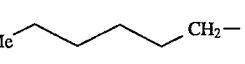 | 142–143° C. |
| 24 | 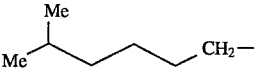 | |

TABLE 2-continued
R¹ = R² = R⁴ = H
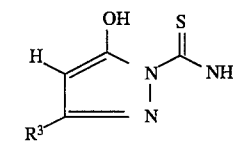
| Ex. No. | R³ | m.p. |
|---|---|---|
| 25 | 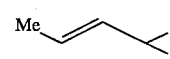 | |
| 26 | 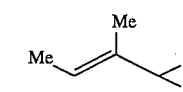 | |
| 27 | 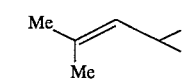 | |
| 28 | 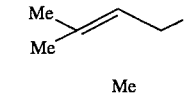 | |
| 29 | 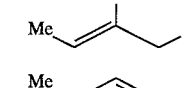 | |
| 30 |  | |
| 31 | 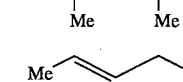 | |
| 32 | 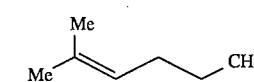 | |
| 33 | 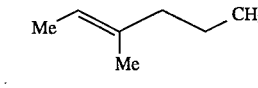 | |
| 34 | 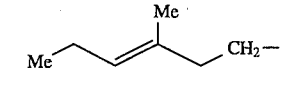 | |
| 35 | NC—CH₂—CH₂— | |
| 36 | CF₃— | 87–88° C. |
| 37 | CF₃—CF₂— | |
| 38 | CF₃—CF₂—CF₂— | |
| 39 | CF₂—CF₂—CH₂— | |
| 40 | CF₃—CF₂—CF₂—CH₂— | |
| 41 | 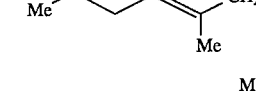 | |
| 42 | 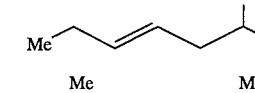 | |
| 43 | 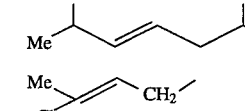 | |
| 44 | 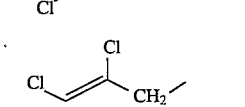 | |
| 45 |  | |
TABLE 2-continued
R¹ = R² = R⁴ = H
| Ex. No. | R³ | m.p. |
|---|---|---|
| 46 | | |
| 47 | | |
| 48 | | |
| 49 | | |
| 50 | | |
| 51 | | |
| 52 | | |
| 53 | | |
| 54 | | |
| 55 | | |
| 56 | | |
| 57 | | |
| 58 | | |
| 59 | | |
| 60 | | |
| 61 | | |

TABLE 2-continued $R^1 = R^2 = R^4 = H$

[Structure: thiosemicarbazone of β-hydroxy-α,β-unsaturated ketone with $R^3$ substituent]

| Ex. No. | $R^3$ | m.p. |
|---|---|---|
| 62 | CCl$_2$=CCl-CH$_2$- (with ethyl) | |
| 63 | (Me)(Cl)C=C(Me)-C(Me)$_2$-CH$_2$- | |
| 64 | (Me)(Cl)C=C(Cl)-CH(Me)- | |
| 65 | Cl$_2$C=C(Cl)-CH(Me)- | |
| 66 | Cl$_2$C=CH-CH(Me)- | |
| 67 | Cl$_2$C=CH-CH$_2$-CH$_2$- | |
| 68 | ClCH=C(Cl)-CH$_2$-CH$_2$- | |
| 69 | Me-CH=C(Cl)-CH(Me)-CH$_2$- | |
| 70 | (Me)(Cl)C=C(Cl)-CH$_2$-CH$_2$- | |
| 71 | (Et)(Cl)C=C(Cl)-CH$_2$-CH$_2$- | |
| 72 | Cl$_2$C=CH-CH$_2$-CH$_2$-CH$_2$- | |
| 73 | ClCH=C(Cl)-CH$_2$-CH$_2$-CH$_2$- | |
| 74 | Me-CH$_2$-C(Cl)=CH-CH$_2$- | |
| 75 | Me-CH$_2$-CH$_2$-C(Cl)=CH-CH$_2$- | |
| 76 | Me-CH=C(Cl)-CH$_2$-CH$_2$-CH(Me)- | |
| 77 | Me-C(Me)=CH-CH(Cl)-CH$_2$-CH$_2$- | |
| 78 | n-C$_7$H$_{15}$ | |
| 79 | n-C$_8$H$_{17}$ | 134–135° C. |
| 80 | n-C$_9$H$_{19}$ | |
| 81 | n-C$_{10}$H$_{21}$ | 154° C. |
| 82 | n-C$_{11}$H$_{23}$ | |
| 83 | n-C$_{12}$H$_{25}$ | |
| 84 | n-C$_{13}$H$_{27}$ | |
| 85 | cyclopentyl | 171° C. |
| 86 | cyclopentenyl | |
| 87 | cyclopentadienyl | |
| 88 | cyclopentyl-CH$_2$- | |
| 89 | cyclopentenyl-CH$_2$- | |
| 90 | cyclopentenyl-CH$_2$- | |
| 91 | cyclohexyl | 154° C. |
| 92 | cyclohexenyl | |

TABLE 2-continued $R^1 = R^2 = R^4 = H$

[Structure: HO-C(=CH-R³)-N(H)-N=... with thiourea group C(=S)NH₂]

| Ex. No. | R³ | m.p. |
|---|---|---|
| 93 | cyclohexyl-CH₂— | |
| 94 | cyclohexenyl-CH₂— | |
| 95 | 3-(CO₂Et)-phenyl | |
| 96 | phenyl | 142–143° C. |
| 97 | 2-Cl-phenyl | |
| 98 | 3-Cl-phenyl | |
| 99 | 4-Cl-phenyl | |
| 100 | 2,4-diCl-phenyl | |
| 101 | 2,3-diCl-phenyl | |
| 102 | 3,4-diCl-phenyl | |
| 103 | 2,5-diCl-phenyl | |
| 104 | 2,6-diCl-phenyl | |
| 105 | 2-F-phenyl | 135–136° C. |
| 106 | 4-Br-phenyl | |
| 107 | 4-F-2-Me-phenyl | |
| 108 | 4-I-phenyl | |
| 109 | 2-CF₃-phenyl | |
| 110 | 2-OMe-phenyl | |

TABLE 2-continued

R¹ = R² = R⁴ = H

[Structure: HO-C(=N-NH-C(=S)-NH₂)-CH=CR³-H]

| Ex. No. | R³ | m.p. |
|---|---|---|
| 111 | 3-MeO-C₆H₄- | |
| 112 | 4-MeO-C₆H₄- | |
| 113 | 2,4-(MeO)₂-C₆H₃- | |
| 114 | 3,4-(MeO)₂-C₆H₃- | |
| 115 | 3-MeO-4-Me-C₆H₃- | |
| 116 | 2-MeO-5-Me-C₆H₃- | |
| 117 | 4-biphenyl- | |
| 118 | 2-biphenyl- | |
| 119 | 1-naphthyl- | |
| 120 | 2-naphthyl- | |
| 121 | 2-Me-C₆H₄- | |
| 122 | 3-Me-C₆H₄- | |
| 123 | 4-Me-C₆H₄- | |
| 124 | 2,3-Me₂-C₆H₃- | |
| 125 | 2,4-Me₂-C₆H₃- | |
| 126 | 3,5-Me₂-C₆H₃- | |
| 127 | 2,6-Me₂-C₆H₃- | |
| 128 | 2,5-Me₂-C₆H₃- | |

TABLE 2-continued

R$^1$ = R$^2$ = R$^4$ = H

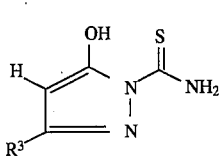

| Ex. No. | R$^3$ | m.p. |
|---|---|---|
| 129 | 3,5-Me$_2$-C$_6$H$_3$- (2,4,6-trimethylphenyl shown as Me, Me, Me on ring) | |
| 130 | C$_6$H$_5$-CH$_2$- | |
| 131 | 2-F-C$_6$H$_4$-CH$_2$- | |
| 132 | 2-Cl-C$_6$H$_4$-CH$_2$- | |
| 133 | 3-Cl-C$_6$H$_4$-CH$_2$- | |
| 134 | 4-Cl-C$_6$H$_4$-CH$_2$- | |
| 135 | 2,4-Cl$_2$-C$_6$H$_3$-CH$_2$- | |
| 136 | 2,3-Cl$_2$-C$_6$H$_3$-CH$_2$- | |
| 137 | 3,4-Cl$_2$-C$_6$H$_3$-CH$_2$- | |
| 138 | 3,5-Cl$_2$-C$_6$H$_3$-CH$_2$- | |
| 139 | 2,5-Cl$_2$-C$_6$H$_3$-CH$_2$- | |
| 140 | 2,6-Cl$_2$-C$_6$H$_3$-CH$_2$- | |
| 141 | 4-Me-C$_6$H$_4$-CH$_2$- | |
| 142 | 3-Me-C$_6$H$_4$-CH$_2$- | |
| 143 | 2-Me-C$_6$H$_4$-CH$_2$- | |
| 144 | 2-OMe-C$_6$H$_4$-CH$_2$- | |
| 145 | 3-OMe-C$_6$H$_4$-CH$_2$- | |
| 146 | 4-OMe-C$_6$H$_4$-CH$_2$- | |
| 147 | 4-$^t$Bu-C$_6$H$_4$-CH$_2$- | |
| 148 | C$_6$H$_5$-CH(Me)- | |

TABLE 2-continued $R^1 = R^2 = R^4 = H$

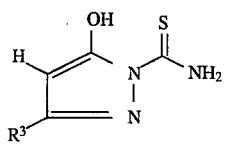

| Ex. No. | R³ | m.p. |
|---|---|---|
| 149 | 4-Cl-C₆H₄-CH(Me)- | |
| 150 | 1-naphthyl-CH₂- | |
| 151 | 2-naphthyl-CH₂- | |
| 152 | Ph-S- | |
| 153 | 4-Cl-C₆H₄-S- | |
| 154 | Ph-O- | |
| 155 | 4-Cl-C₆H₄-O- | |
| 156 | Ph-CH₂-S- | |
| 157 | Ph-CH₂-O- | |
| 158 | 4-Cl-C₆H₄-CH₂-S- | |
| 159 | MeO-C(O)- | |
| 160 | EtO-C(O)- | |
| 161 | n-Pr-C(O)- | |
| 162 | n-Bu-C(O)- | |
| 163 | Me—O— | |
| 164 | Et—O— | |
| 165 | n-Pr—O— | |
| 166 | n-Bu—O— | |
| 167 | Me—S—CH₂— | |
| 168 | Et—S—CH₂— | 118–119° C. |
| 169 | n-Pr—S—CH₂— | |
| 170 | n-Bu—S—CH₂— | |
| 171 | i-Pr—S—CH₂— | |
| 172 | n-C₅H₄—S—CH₂ | |
| 173 | Me—S—(CH₂)₂— | |
| 174 | Et—S—(CH₂)₂— | |
| 175 | n-Pr—S—(CH₂)₂— | |
| 176 | n-Bu—S—(CH₂)₂— | |
| 177 | Me—O—CH₂— | |
| 178 | Et—O—CH₂— | |
| 179 | n-Pr—O—CH₂— | |
| 180 | n-Bu—O—CH₂— | |
| 181 | n-Pr—O—CH₂— | |
| 182 | n-C₅H₄—O—CH₂— | |
| 183 | Me—O—(CH₂)₂— | 140° C. |
| 184 | Et—O—(CH₂)₂— | |
| 185 | n-Pr—O—(CH₂)₂— | |
| 186 | n-Bu—O—(CH₂)₂— | |
| 187 | Ph—S—CH₂— | |
| 188 | Ph—O—CH₂— | 178.6° C. |
| 189 | Ph—CH₂—S—CH₂— | |
| 190 | Ph—CH₂—O—CH₂— | |
| 191 | MeO-C(O)-CH₂- | 142° C. |
| 192 | EtO-C(O)-CH₂- | 138° C. |
| 193 | 4-F-C₆H₄- | 145–6° C. |
| 194 | 2-furyl- | 152° C. |
| 195 | 2-thienyl- | |
| 196 | 3-furyl- | |

TABLE 2-continued $R^1 = R^2 = R^4 = H$

[Structure: OH and S substituted vinyl-thiourea with R³ and N-N]

| Ex. No. | R³ | m.p. |
|---|---|---|
| 197 | 3-methylthiophene | |
| 198 | 2,5-dimethylfuran (Me—O—Me) | |
| 199 | 2,5-dimethylthiophene (Me—S—Me) | |
| 200 | Cl-pyrazole | |
| 201 | Br—C₆H₄—CH₂— | |
| 202 | 2-Br-phenyl | |
| 203 | 4-F-phenyl | |
| 204 | 3-phenoxyphenyl | |
| 205 | n-C₁₇—H₃₉ | |
| 206 | EtO-C(O)-CH₂-CH₂- | 130° C. |
| 207 | Me-CH(Me)-CH₂- | |

The numbering of the examples below follows the preceding Tables 1 and 2 and is composed of Table Number/Example Number.

Examples (3,4-disubstituted compounds)

Tables 3–8

Example 3 from Table 3

A mixture of 3.9 g (0.025 mol) of ethyl 2-ethyl-acetoacetate, 2.3 g (0.025 mol) of thiosemicarbazide and 100 ml of ethanol is held at reflux temperature for 3 hours with stirring. The reaction mixture is then cooled to 20° C., and 2.9 g (0.025 mol; 97%) of potassium tertbutylate are added in portions with stirring. The resulting suspension is then stirred for 3 hours at 20°–30° C. and subsequently stirred into dilute hydrochloric acid (500 ml of water/20 ml of conc. HCl), and the precipitate is filtered off with suction. It is washed thoroughly with water and dried under hot conditions until constant weight is reached.

Yield: 2.9 g (82.5% of theory) m.p.: 163° C.

In the same way, from the corresponding α-substituted β-keto esters, the 3,4-disubstituted 1-thiocarbamoyl-5-hydroxypyrazoles listed in the following Tables 3–8 and 65 can be obtained.

TABLE 3

$R^1 = R^2 = H$
$R^3 = Me$
$R^4 =$ see Table 1

[Structure with R⁴, OH, S, NH₂, N-N, Me]

| | |
|---|---|
| 3/002 | m.p.: 164° C. |
| 3/035.H₂O | m.p.: 153° C. |
| 3/130 | m.p.: 160° C. |
| 3/148 | m.p.: 142–143° C. |
| 3/003 | m.p.: 163° C. |
| 3/007 | m.p.: 139° C. |
| 3/042 | m.p.: 148° C. |
| 3/078 | m.p.: 124° C. |
| 3/083 | m.p.: 112° C. |
| 3/023 | m.p.: 144° C. |
| 3/005 | m.p.: 137° C. |

TABLE 4

$R^1 = R^2 = H$
$R^3 =$ Table 1
$R^4 = Me$

[Structure with Me, OH, S, NH₂, N-N, R³]

| | |
|---|---|
| 4/003 | m.p.: 152–153° C. |
| 4/004 | m.p.: 123° C. |
| 4/007 | m.p.: 131° C. |
| 4/011 | m.p.: 120° C. |

Table 5=Table 3 but R³=Et
Table 6=Table 3 but R³=n-Pr
Table 7=Table 4 but R⁴=Et
Table 8=Table 4 but R⁴=n-Pr
Tables 9 to 16 analogous to 1–8 but R¹=Me
Tables 17 to 32 analogous to 1–8 but R¹=R²=Me
Tables 33 to 48 analogous to 1–8 but R¹=allyl

Tables 49 to 64 analogous to 1–8 but $R^1$=phenyl

| No. | m.p. | Structure |
|---|---|---|
| 49/002 | m.p.: 204–205° C. | (OH, Me, N-N, NHPh, C=S) |
| 10/002 | m.p.: 210° C. decomp. | (OH, Me, N-N, NHMe, C=S) |
| 9/192 | m.p.: 176° C. | (EtO-C(=O), OH, N-N, NHMe, C=S) |
| 16/003 | m.p.: 74–75° C. | (Me-CH2, OH, N-N, NHMe, C=S) |
| 17/130 | m.p.: 181° C. | (PhCH2, OH, N-N, NHMe, C=S) |
| 11/023 | m.p.: 87–88° C. | (n-C6H13, Me, OH, N-N, NHMe, C=S) |
| 10/007 | m.p.: 147° C. | (OH, N-N, NHMe, C=S, alkyl chain) |
| 9/079 | m.p.: 117° C. | (C8H17, OH, N-N, NHMe, C=S) |
| 49/079 | m.p.: 153–156° C. | (C8H17, OH, N-N, NHPh, C=S) |
| 51/003 | m.p.: 175° C. | (Et, Me, OH, N-N, NH-Ph, C=S) |
| 33/079 | m.p.: 71–72° C. | (C8H17, OH, N-N, NH-CH2-CH=CH2, C=S) |
| 49/007 | m.p.: 209–210° C. | (C4H9, OH, N-N, NH-Ph, C=S) |
| 9/007 | m.p.: 134° C. | (C4H9, OH, N-N, NH-Me, C=S) |
| 33/007 | m.p.: 80–81° C. | (C4H9, OH, N-N, NH-CH2CH=CH2, C=S) |
| 15/002 | m.p.: 153–154° C. | (Et, Me, O, N-N, NMe, C=S, H) |
| 34/007 | m.p.: 92° C. | (OH, C4H9, N-N, NH-CH2CH=CH2, C=S) |

Examples for Table 65

If $R^3$ and $R^4$ represent a saturated chain, preparation is as for Tables 3 to 8; for unsaturated compounds derived from imidazolinone it is as follows:

13.8 g of ethyl 2-chloro-3,5-dinitrobenzoate, 60 ml of ethanol and 13.7 g of thiosemicarbazide are stirred at 25° C. for 54 h, and then, by filtering off the mother liquor with suction, 22 g of (structure: O2N, NO2-substituted phenyl with OH, N-N, NH2, C=S)

of melting point 153° C. are isolated, or 4.2 g of imidazolinone and 5.0 g of phenyl mustard oil are refluxed in toluene for 3 h and the crystals which separate out on cooling are isolated: 0.6 g, m.p.=194° C., decomposition.

(structure: benzene ring with OH, N-N, NH-Ph, C=S)

For compounds of this type, the keto form is also a particularly relevant species.

TABLE 65

R³ and R⁴ form a ring
R¹ and R²: see Examples

| No. | Structure | m.p. |
|---|---|---|
| 65/001 | OH/S, NH₂ (phenyl) | |
| 65/002 | O₂N, NO₂ substituted | m.p.: 153° C. |
| 65/003 | NH-phenyl | m.p.: 194° C. (decomp.) |
| 65/004 | NH—Me | m.p.: 199° C. |
| 65/006 | NH—CH₂—CH=CH₂ | m.p.: 160° C. |
| 65/007 | Me-cyclohexyl, NH₂·H₂O | m.p.: 173° C. |
| 65/008 | cyclohexyl, NH₂·H₂C | m.p.: 148° C. |
| 65/009 | cyclohexyl, NH₂ | m.p.: 179–180° C. |
| 65/010 | S-cyclic, NH₂ | m.p.: 102–103° C. |
| 65/011 | Me-cyclohexyl, NH₂ | m.p.: 176° C. |

TABLES 66–130

As Tables 1–65, but in each case complexes with metals; see Examples

| No. | | m.p. |
|---|---|---|
| 66/007 | .2H₂O.½Zn | m.p.: 189–192° C. |
| 66/130 | .½Zn | m.p.: 160° C. |
| 66/007 | .½Zn | m.p.: 178–180° C. |

Preparation of compounds from Tables 131–139:

Example No. 131/007

10.0 g (0.05 mol) of 86% ethyl α-formyl-hexanoate and 5.3 g (0.05 mol) of thiocarbohydrazide are refluxed for 3.5 hours in 100 ml of ethanol, and subsequently 5.8 g (0.05 mol) of potassium tert-butylate are added at 25° C. After stirring overnight, evaporation of the solvent in a rotary evaporator and addition of 200 ml of water, filtration with suction is carried out, the filtrate is drawn up with suction, and filtration with suction is repeated.

1.0 g of 131/007 is obtained with a melting point of 116°–118° C.

TABLES 131–139

As Tables 1–8 or 65, but with the following basic structure:

$$\text{R}^4, \text{R}^3 \text{ substituted with OH, S, NH—NH}_2$$

| No. | Structure | m.p. |
|---|---|---|
| 131/007 | m.p.: 116–118° C. | |
| 133/007 | ⁿBn, NH—NH₂ | m.p.: 160–165° C. |
| | ⁿBn, H₃C, NH—NH₂ | |
| 139/009 | cyclohexyl, NH, NH₂ | m.p.: 129–130° C. |

We claim:

1. Compounds of the formula (I)

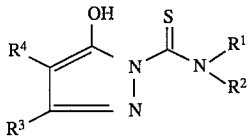

(I)

in which
R¹ and R² denote hydrogen,
R³ denotes substituted alkyl or aralkyl, and
R⁴ denotes hydrogen or unsubstituted or substituted alkyl or aralkyl.

2. A compound of the formula

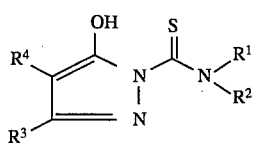

(II)

in which
- $R^1$ and $R^2$ denote H, alkenyl or aryl, with the proviso that
- $R^1$ and $R^2$ are not simultaneously hydrogen and $R^1$ or $R^2$ are not allyl, and
- $R^3$ represents substituted alkyl or unsubstituted or substituted alkenyl, alkinyl, cycloalkyl, cycloalkenyl, alkyl (cycloalkyl), alkenyl (cycloalkenyl), alkoxy, alkylthio, aralkoxy, aralkylthio, aralkyl, aryl, hetaryl, aryloxy, hetaryloxy, arylthio, hetarylthio, alkoxycarbonyl, alkoxycarbonyl alkyl or cyanoalkyl,
- $R^4$ represents hydrogen, or unsubstituted or substituted alkyl, alkenyl, alkinyl, cycloalkyl, cycloalkenyl, alkyl (cycloalkyl), alkenyl (cycloalkenyl), alkoxy, alkylthio, aralkoxy, aralkylthio, aralkyl, aryl, hetaryl, aryloxy, hetaryloxy, arylthio, hetarylthio, alkoxycarbonyl, alkoxycarbonyl alkyl or cyanoalkyl, or
- $R^3$ and $R^4$ form a saturated or partially or completely unsaturated unsubstituted or substituted ring of 5 to 9 atoms in total, all of which are carbon atoms except for a maximum of two nitrogens, sulphur or oxygen atoms, or their metal complexes.

3. A compound of the formula

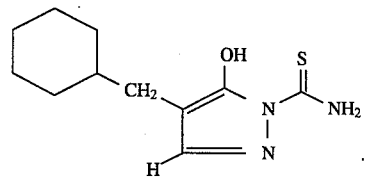

4. A pharmaceutical composition comprising as the active ingredient, a compound according to claim 1 and a diluent.

5. A pharmaceutical composition comprising as the active ingredient, a compound according to claim 2 and a diluent.

6. A pharmaceutical composition comprising as the active ingredient, a compound according to claim 3 and a diluent.

* * * * *